US008697357B2

(12) United States Patent
Fujimoto et al.

(10) Patent No.: US 8,697,357 B2
(45) Date of Patent: Apr. 15, 2014

(54) METHOD FOR DETECTION OF METHYLCYTOSINE USING PHOTORESPONSIVE PROBE

(75) Inventors: Kenzo Fujimoto, Nomi (JP); Masayuki Ogino, Nomi (JP); Yuta Taya, Nomi (JP)

(73) Assignee: Japan Advanced Institute of Science and Technology, Nomi-shi (JP)

( * ) Notice: Subject to any disclaimer, the term of this patent is extended or adjusted under 35 U.S.C. 154(b) by 489 days.

(21) Appl. No.: 12/922,025

(22) PCT Filed: Mar. 11, 2009

(86) PCT No.: PCT/JP2009/001090
§ 371 (c)(1),
(2), (4) Date: Nov. 11, 2010

(87) PCT Pub. No.: WO2009/113303
PCT Pub. Date: Sep. 17, 2009

(65) Prior Publication Data
US 2011/0091887 A1 Apr. 21, 2011

(30) Foreign Application Priority Data
Mar. 12, 2008 (JP) ................ 2008-063290

(51) Int. Cl.
*C12Q 1/68* (2006.01)
*C07H 21/00* (2006.01)
(52) U.S. Cl.
USPC .......................... 435/6.1; 536/23.1
(58) Field of Classification Search
USPC .......................... 435/6.1; 536/23.1
See application file for complete search history.

(56) References Cited
U.S. PATENT DOCUMENTS

| 4,267,171 | A | 5/1981 | Bergstrom et al. |
| 5,043,510 | A | 8/1991 | Casalnuovo et al. |
| 5,215,971 | A | 6/1993 | Datema et al. |
| 5,484,908 | A | 1/1996 | Froehler et al. |
| 5,645,985 | A | 7/1997 | Froehler et al. |
| 5,830,653 | A | 11/1998 | Froehler et al. |
| 6,235,887 | B1 | 5/2001 | Froehler et al. |
| 6,380,368 | B1 | 4/2002 | Froehler et al. |
| 2003/0096980 | A1 | 5/2003 | Froehler et al. |
| 2003/0170680 | A1 | 9/2003 | Froehler et al. |
| 2004/0220395 | A1 | 11/2004 | Froehler et al. |

FOREIGN PATENT DOCUMENTS

| JP | 1-501551 A | 6/1989 |
| JP | 4-077439 A | 3/1992 |
| JP | 7-501527 A | 2/1995 |
| WO | 88-04662 A1 | 6/1988 |
| WO | 93-10820 A1 | 6/1993 |
| WO | 2005/021568 A2 | 3/2005 |
| WO | 2006-137190 A1 | 12/2006 |
| WO | 2007/058326 A1 | 5/2007 |

OTHER PUBLICATIONS

Ding, H. et al., "Hole Migration is the Major Pathway Involved in Alkali-Labile Lesion Formation in DNA by the Direct Effect of Ionizing Radiation", Journal of the American Chemical Society, Jan. 4, 2007, p. 772-773, vol. 129, No. 4.
Ding, Y. et al., "Synthesis of 2'-0-methyl-5-alkynyl and alkenyl substituted uridine derivatives to screen for inhibitors of HCV", Heterocycles, Feb. 14, 2006, p. 521-530, vol. 68, No. 3.
Aucagne, V. et al., "Palladium-Catalyzed Synthesis of Uridines on Polystyrene-Based Solid Supports", Journal of Combinatorial Chemistry, Jun. 23, 2004, p. 717-723, vol. 6, No. 5.
Gupta, S. et al, "Applications of graph theory: Relationship of molecular connectivity index and atomic molecular connectivity index with anti-HSV activity", Theochem, Aug. 27, 2001, p. 147-152, vol. 571.
Poznanski, J. et al., "IH NMR conformational study of antiherpetic C5-substituted 2'-deoxyuridines: insight into the nature of structure-activity relationships", Biochemical and Biophysical Research Communications, May 2000, p. 64-74, vol. 272, No. 1.
Selvidge, S.D. et al., "Synthesis of 5-formyluridines", Nucleosides & Nucleotides, Oct. 1997, p. 2019-2024, vol. 16, No. 10 & 11.
Yamaguchi, T. et al., "Synthesis and utilization of a photolabile oligodeoxyribonucleotide probe bearing an aryl (trifluoromethyl) diazirine moiety", Nucleic Acids Symposium Series No. 35, 1996, p. 237-238.
Cserhati, T. et al., "Inclusion complex formation of antisense nucleotides with hydroxypropyl P-cyclodextrin", International Journal of Pharmaceutics, Sep. 6, 1996, p. 1-7, vol. 141.
Yamaguchi, T. et al., "Synthetic nucleoside and nucleotides. XXXIV. Photoaffinity labeling of HIV reverse transcriptase: synthesis and utilization of 2',3'-dideoxy uridylate analogs bearing aryl(trifluoromethyl)diazirine moiety", Nucleosides & Nucleotides, Jan. 1996, p. 607-618, vol. 15, No. 1-3.
Matsuhashi, H. et al., "Synthesis of 5-substituted pyrimidine nucleosides through a palladiumcatalyzed cross-coupling of alkenylhalosilanes", Heterocycles, Jan. 1, 1996, p. 375-84, vol. 42, No. 1.
Cserhati, T. et al., "Thin layer chromatography and principal component analysis for the study of the interaction of amino acids with some antisense nucleosides", Analytica Chimica Acta, Nov. 20, 1995, p. 105-10, vol. 316.

(Continued)

*Primary Examiner* — Jezia Riley
(74) *Attorney, Agent, or Firm* — Westerman, Hattori, Daniels & Adrian, LLP

(57) ABSTRACT

The present invention provides a method for detecting methylcytosine in DNA rapidly, conveniently, and with high sensitivity. The present invention relates to a method for detecting methylcytosine by using a methylcytosine photocoupling agent (a photoresponsive probe) consisting of nucleic acids having a group represented by the Formula (I), (II), (III) or (IV) as a base moiety.

7 Claims, 1 Drawing Sheet

(56) References Cited

OTHER PUBLICATIONS

Kalman, A. et al., "Crystal structure of (E)-5-(1-butenyl)-2'-deoxyuridine, C13,H18,N2,O5", Zeitschrift fur Kristallographie, 1995, p. 713-14, vol. 210, No. 9.

Molina, M.J. et al., "Theoretical studies of 5-X-2'-deoxyuracils with known antiviral activity. Part 2. A comparison of molecular mechanics, AM1, and PM3 methodologies", Journal of Molecular Structure (THEOCHEM), Mar. 20, 1995, p. 111-19, vol. 333, No. 1-2.

Yamaguchi, T. et al., "Utilization of photoreactive 2'-deoxy-5-styryluridylic acid analog as a photoaffinity labeling for HIV-1 reverse transcriptase", Nucleic Acids Symposium Series No. 31, 1994, p. 287-8.

Yamaguchi, T. et al., "Synthetic nucleosides and nucleotides. XXXI. Inhibitory effects of 2'-deoxy-5-styryluridine 5'-triphosphate analogs on retroviral reverse transcriptases and higher eukaryotic DNA polymerases", Nucleosides & Nucleotides, Jul. 1994, p. 1247-1258, vol. 13, No. 6-7.

Czernecki, S. et al., "Carbometallation of 5-ethynyl-pyrimidine-2'-deoxy nucleosides: preparation of 5-(1-[E]-butenyl)- and 5-(3-[E]-3-enyl)-2'-deoxyuridine", Tetrahedron Letters, May 23, 1994, p. 3539-42, vol. 35, No. 21.

Mendiratta, S. et al., "Structure-Activity Study on Antiviral 5-Vinylpyrimidine Nucleoside Analogs Using Wiener's Topological Index", Journal of Chemical Information and Computer Sciences, Jul. 1994, p. 867-71, vol. 34, No. 4.

Molina, M.J. et al., "Structural study of P-D-arabinofuranosyluracil derivatives with known antiviral activity. Part 2. Molecular mechanics and molecular orbital (MNDO, AM1 and PM3) calculations: a comparative study", Journal of Molecular Structure (THEOCHEM), Mar. 10, 1994, p. 35-53, vol. 305.

Hirota, K. et al., "Facile synthesis of thymidine derivatives by cross-coupling of 5-halogenouridine derivatives with trimethylaluminum", Synthesis, Feb. 1993, p. 213-15, No. 2.

Yamaguchi, T. et al., "Inhibitory effects of 2'-deoxy-5-styryluridine 5'-triphosphate analogs on retroviral reverse transcriptase and eukaryotic DNA polymerases", Nucleic Acids Symposium Series, 1992, p. 191-2, vol. 27.

Valko, K. et al., "Relationships between nucleotide incorporation rates and molecular parameters obtained by molecular modelling and chromatography", Journal of Pharmaceutical and Biomedical Analysis, Apr. 28, 1991, p. 1125-31 vol. 9, No. 10-12.

Yamaguchi, T. et al., "Synthetic nucleosides and nucleotides. XXX. Synthesis and antiviral activity of 3'-azido, 2',3'—unsaturated and 2',3'-dideoxy derivatives of E-5-styryl-2'-deoxyuridine on human immunodeficiency virus", Nucleosides & Nucleotides, Feb. 1992, p. 373-82, vol. 11, No. 2-4.

Hassan, M.E., "Cytidine nucleosides. II. Photochemical synthesis of 5-alkylcytidine nucleosides", Chemical Papers, Oct. 1991, p. 697-702, vol. 45, No. 5.

Whale, R.F. et al., "The synthesis of some 5-vinyluracil nucleoside analogs", Nucleosides & Nucleotides, Oct. 1991, p. 1615-24, vol. 10, No. 7.

Hassan, M.E., "Palladium-catalyzed cross-coupling reaction of organostannanes with nucleoside halides", Collection of Czechoslovak Chemical Communications, Sep. 1991, p. 1944-7, vol. 56, No. 9.

Cserhati, T., "Retention behavior of some synthetic nucleosides on cyano (CN), diol, and amino (NH2) precoated high-performance thin-layer chromatographic plates", Journal of Chromatographic Science, May 1991, p. 210-16 vol. 29, No. 5.

Cserhati, T. et al., "Hydrophobic interaction between tryptophan and some synthetic nucleosides", Biochemistry International, Mar. 1991, p. 987-97, vol. 23, No. 5.

Valko, K. et al., "Comparative investigation of the retention behavior of nucleoside derivatives on alumina stationary phases in thin-layer chromatography and high performance liquid chromatography", Journal of Chromatography, 1991, p. 667-75, vol. 550, No. 1-2.

Eriksson, S. et al., "Comparison of the substrate specificities of human thymidine kinase 1 and 2 and deoxycytidine kinase toward antiviral and cytostatic nucleoside analogs", Biochemical and Biophysical Research Communications, Apr. 30, 1991, p. 586-92, vol. 176, No. 2.

Hassan, M.E., "A new palladium-catalyzed coupling reaction of vinylic and allylic triflates with pyrimidine nucleosides", Canadian Journal of Chemistry, Feb. 1991, p. 198-200 vol. 69, No. 2.

Olofsson, S. et al., "New virus-selective inhibitor of terminal glycosylation increasing immunological reactivity of a viral glycoprotein", Antiviral Chemistry & Chemotherapy, Jan. 1990, p. 17-24, vol. 1, No. 1.

Cserhati, T. et al., "Relationship between the hydrophobic and hydrophilic molecular parameters of some synthetic nucleosides, determined by means of adsorptive and reversed-phase thin-layer chromatography", Journal of Biochemical and Biophysical Methods, Jan. 1990, p. 81-95, vol. 20, No. 2.

Valko, K. et al., "Application of chromatographic retention data in an investigation of a quantitative structure-nucleotide incorporation rate relationship", Journal of Chromatography, May 11, 1990, p. 35-44, vol. 506.

Casalnuovo, A.L. et al., "Palladium-catalyzed alkylations in aqueous media", Journal of the American Chemical Society, May 1990, p. 4324-30, vol. 112, No. 11.

Valko, K. et al., "Correlation of nucleotide incorporation rate and HPLC retention parameters of substituted nucleosides", Journal of Liquid Chromatography, 1989, p. 2103-16, vol. 12, No. 11.

Izuta, S. et al., "Synthetic nucleosides and nucleotides. XXVII. Selective inhibition of deoxyribonucleic acid polymerase a 1-b-D-arabinofuranosyl-5-styryluracil 5'-triphosphates and related nucleotides: influence of hydrophobic and steric factors on the inhibitory action", Chemical & Pharmaceutical Bulletin, Dec. 1987, p. 4829-38, vol. 35, No. 12.

Hirota, K. et al., "A simple synthesis of 5-(1-alkenyl)uracil derivatives by palladium catalyzed oxidative coupling of uracils with olefins", Synthesis, May 1987, p. 495-6, No. 5.

Goodchild, J. et al., "The carbocyclic analog of 5-(1-propenyl)-2'-deoxyuridine. Synthesis and anti-herpes activity", Nucleosides & Nucleotides, Dec. 1986, p. 571-8, vol. 5, No. 5.

Vincent, P. et al., "Synthesis and biological activities of new (E)-5-alkynyl-2'-deoxyuridines", Nucleosides & Nucleotides, Sep. 1985, p. 447-63, vol. 4, No. 4.

Balzarini, J. et al., "Incorporation of 5-substituted pyrimidine nucleoside analogs into DNA of a thymidylate synthetase-deficient murine FM3A carcinoma cell line", Methods and Findings in Experimental and Clinical Pharmacology, Jan. 1985, p. 19-28, vol. 7, No. 1.

Sim, I.S. et al., "5-Substituted deoxyuridines—structural requirements for antiviral activity against herpes simplex virus types 1 and 2 and possible biochemical basis for relative potency", Antiviral Research, Jun. 1984, p. 159-68, vol. 4, No. 3.

Crow, F.W. et al., "Fast atom bombardment combined with tandem mass spectrometry for the determination of nucleosides", Analytical Biochemistry, May 15, 1984, p. 243-62, vol. 139, No. 1.

Cassiman, J.J. et al., "Induction of sister-chromatid exchange by 5-substituted 2'-deoxyuridines", Mutation Research, Genetic Toxicology Testing, May-Jun. 1983, p. 317-27, vol. 117, No. 3-4.

Goodchild, J. et al., "Structural requirements of olefinic 5-substituted deoxyuridines for antiherpes activity", Journal of Medicinal Chemistry, Sep. 1983, p. 1252-7, vol. 26, No. 9.

Robins, M.J. et al., "Nucleic acid related compounds. 39. Efficient conversion of 5-iodo to 5-alkynyl and derived 5-substituted uracil bases and nucleosides", Journal of Organic Chemistry, Jun. 1983, p. 1854-62, vol. 48, No. 11.

Balzarini, J. et al., "Structure-function relationship of the antitumor cell activity of pyrimidine and pyridine derivatives", Proceedings of the 4th International Round Table on Nucleosides, Nucleotides, and Their Biological Applications, 1982, p. 275-91.

De Clercq, E. et al., "Nucleic acid related compounds. 40. Synthesis and biological activities of 5-alkynyluracil nucleosides", Journal of Medicinal Chemistry, May 1983, p. 661-6, vol. 26, No. 5.

Sim, I.S. et al., "Possible molecular basis for antiviral activity of certain 5-substituted deoxyuridines", Antimicrobial Agents and Chemotherapy, Mar. 1983, p. 416-21, vol. 23, No. 3.

Balzarini, J. et al., 5-Substituted 2'-deoxyuridines: correlation between inhibition of tumor cell growth and inhibition of thymidine

(56) References Cited

OTHER PUBLICATIONS kinase and thymidylate synthetase, Biochemical Pharmacology, Nov. 15, 1982, p. 3673-82, vol. 31, No. 22.
International Search Report of PCT/JP2009/001090, Mailing Date of Apr. 28, 2009.
European Office Action dated Feb. 27, 2012, issued in corresponding European Patent Application No. 09720175.0.
Matsumura et al.; "Photochemical transition of 5-methylcytosine to thymine by DNA photoligation"; Oxford University Press 2007, Nucleic Acids Symposium Series No. 51, pp. 233-234.(cited in European Office Action dated Feb. 27, 2012).
Bergstrom, Donald E. et al; "Antiviral Activity of C-5 Substituted Tubercidin Analogues"; Journal of Medicinal Chemistry, American Chemical Society, US, vol. 27, Jan. 1, 1984, pp. 285-292, XP002277617.(cited in Supplementary European Search Report dated Jul. 11, 2011).
Ogino, Masayuki et al.; "Photochemical Synthesis of R-Shaped DNA towards DNA Recombination and Processing In Vitro"; Angewandte Chemie International Edition, vol. 45, No. 43, Nov. 6, 2006, pp. 7223-7226, XP55001183. (cited in Supplementary European Search Report dated Jul. 11, 2011).
Kyoung, Roh R. et al.; "Palladium Catalyzed Alkenylation or Alkynylation at C-5 of Uracil Nucleosides Using Novel Phenyliodonium Triflate"; Tetrahedron Letters, Elsevier, Amsterdam, NL, vol. 40, No. 10, Mar. 5, 1999, pp. 1903-1906, XP004155994.(cited in Supplementary European Search Report dated Jul. 11, 2011).
Supplementary European Search Report dated Jul. 11, 2011, issued in corresponding European Patent Application No. 09720175.0.
Yoshimura, Yoshinaga et al.; "Highly Selective and Sensitive Template-Directed Photoligation of DNA via 5-Carbamoylvinyl-2'-deoxycytidine"; Organic Letters, vol. 8, No. 22, Oct. 1, 2006, pp. 5049-5051, XP55001185. (cited in Supplementary European Search Report dated Jul. 11, 2011).
Vincent, P. et al., "E-5-alkenyl-2'-deoxyuridines by coupling of alkenyl organozirconiums with 5-iodo-0-3',5'-bis (trimethylsilyl)deoxyuridine, catalyzed by organopalladium complexes", Tetrahedron Letters, Jan. 1982, p. 63-4, vol. 23, No. 1.
Hampton, A. et al., "Species- or isozyme-specific enzyme inhibitors. 5. Differential effects of thymidine substituents on affinity for rat thymidine kinase isozymes", Journal of Medicinal Chemistry, Jun. 1982, p. 644-9, vol. 25, No. 6.
Bigge, C.F. et al., "Palladium(II) catalyzed coupling reactions of polyuridylic acid and uridylyl(3'® 5')uridine with styrene and 3-nitrostyrene", Journal of Carbohydrates, Nucleosides, Nucleotides, 1981, p. 295-313, vol. 8, No. 4.
Stening, G. et al., "Antiherpes activity of [E]- 5-(1-propenyl)-2'-deoxyuridine and 5-(1-propenyl)-1-b-D-arabinofuranosyluracil", Antiviral Research, Nov. 1981, p. 213-23, vol. 1, No. 4.
Kulikowski, T. et al., "Pyrimidine arabinofuranosyl nucleosides with 5-substituted long, branched and unsaturated chains: synthesis and antiherpes properties", Nucleic Acids Research, Symposium Series, Jan. 1981, p. 103-6, No. 9.
De Clercq, E. et al., "Differential inhibition of herpes simplex viruses, type 1 (HSV-1) and type 2 (HSV-2), by (E)-5-(2-X-vinyl)-2'-deoxyuridines", Acta Microbiologica Academiae Scientiarum Hungaricae, 1981, p. 307-12, vol. 28, No. 3.
Bergstrom, D.E. et al., "C-5-Substituted pyrimidine nucleosides. 3. Reaction of allylic chlorides, alcohols, and acetates with pyrimidine nucleoside derived organopalladium intermediates", Journal of Organic Chemistry, Mar. 1981, p. 1432-41, vol. 46, No. 7.
Bergstrom, D.E. et al., "Pyrrolo[2,3-dlpyrimidine nucleoside antibiotic analogs. Synthesis via organopalladium intermediates derived from 5-mercuritubercidin", Journal of Organic Chemistry, Mar. 1981, p. 1423-31, vol. 46, No. 7.
Cheng, Y. et al., "Anti-herpes simplex virus and anti-human cell growth activity of E-5-propenyl-2'-deoxyuridine and the concept of selective protection in antivirus chemotherapy", Antimicrobial Agents and Chemotherapy, Dec. 1980, p. 957-61, vol. 18, No. 6.
Machida, H. et al., "Antiherpesviral activity and inhibitory action on cell growth of 5-alkenyl derivatives of 1-b-D-arabinofuranosyluracil", Antimicrobial Agents and Chemotherapy, Jun. 1980, p. 1030-1, vol. 17, No. 6.
Nakayama, C. et al., "Thymidine phosphorylase. Substrate specificity for 5-substituted 2'-deoxyuridines", Journal of Medicinal Chemistry, Aug. 1980, p. 962-4, vol. 23, No. 8.
Bigge, C.F. et al., "Palladium-catalyzed coupling reactions of uracil nucleosides and nucleotides", Journal of the American Chemical Society, Mar. 1980, p. 2033-8, vol. 102, No. 6.
Bigge, C.F. et al., "Synthesis of 5-styryl derivatives of uracil nucleosides and nucleotides", Tetrahedron Letters, May 1979, p. 1653-6, vol. 20, No. 19.
Bergstrom, D.E. et al., "C-5 substituted pyrimidine nucleosides. 2. Synthesis via olefin coupling to organopalladium intermediates derived from uridine and 2'-deoxyuridine", Journal of the American Chemical Society, Dec. 1978, p. 8106-12, vol. 100, No. 26.
Ruth, J.L. et al., "C-5 substituted pyrimidine nucleosides. 1. Synthesis of C-5 allyl, propyl, and propenyl uracil and cytosine nucleosides via organopalladium intermediates", Journal of Organic Chemistry, Jul. 1978, p. 2870-6, vol. 43, No. 14.
Ogino, M. et al., "Highly selective detection of 5-methylcytosine using photochemical ligation", Chemical Communications (Cambridge, United Kingdom), Dec. 2008, p. 5996-5998, No. 45.
Kyoi, Yoshiaki et al., "Hikari Otesei Cytosine Yudotai o Mochiita DNA-Enkitagata no Kenshutsu", The Chemical Society of Japan Koen Yokoshu, Mar. 12, 2007, p. 1292, vol. 87, No. 2.
Ogino, Masayuki et al., "DNA Hikari Ligation ni yoru RNA Mattan Labeling", The Chemical Society of Japan Koen Yokoshu, Mar. 12, 2008, p. 1527, vol. 88, No. 2.
Farina, V. et al., The Stille Reaction Chapter 1, Organic Reactions (Hoboken, NJ, United States), Apr. 1997, pp. 1-652, vol. 50. Part 1.
Farina, V. et al., The Stille Reaction Chapter 1, Organic Reactions (Hoboken, NJ, United States), Apr. 1997, pp. 1-652, vol. 50. Part 2.
Farina, V. et al., The Stille Reaction Chapter 1, Organic Reactions (Hoboken, NJ, United States), Apr. 1997, pp. 1-652, vol. 50. Part 3.
Farina, V. et al., The Stille Reaction Chapter 1, Organic Reactions (Hoboken, NJ, United States), Apr. 1997, pp. 1-652, vol. 50. Part 4.
Farina, V. et al., The Stille Reaction Chapter 1, Organic Reactions (Hoboken, NJ, United States), Apr. 1997, pp. 1-652, vol. 50. Part 5.
Farina, V. et al., The Stille Reaction Chapter 1, Organic Reactions (Hoboken, NJ, United States), Apr. 1997, pp. 1-652, vol. 50. Part 6.
Larsson, A. et al., "Selectivity of antiherpes compounds on viral and cellular DNA synthesis", International Congress Series (Herpesvirus): Clinical Pharmacology, 1982, p. 211-14, vol. 571.

a) 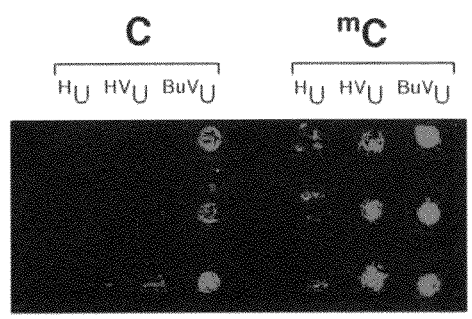 b) 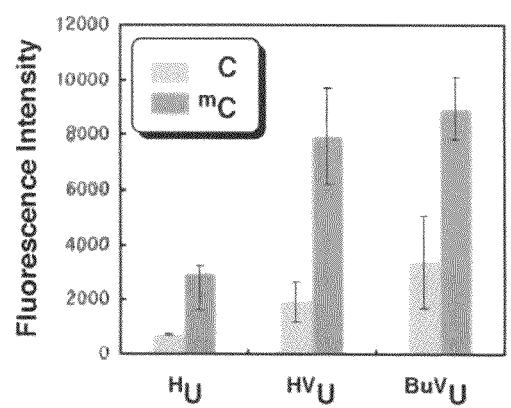

METHOD FOR DETECTION OF METHYLCYTOSINE USING PHOTORESPONSIVE PROBE

TECHNICAL FIELD

The present invention relates to a method for detecting methylcytosine using a photoresponsive probe (agent for photocoupling methylcytosine).

BACKGROUND ART

DNA methylation is a reaction occurring in "cytosine", which is one of the bases constituting DNA. It controls when and from which gene a protein should be produced and also correctly regulates a step of transcription into RNA that is required for protein synthesis. The methylation of cytosine (production of 5-methylcytosine) plays a role of inactivating a gene function, for example, without depending on a nucleotide sequence of the gene. It is known that even cancer might be caused when an abnormality occurs in methylation. From the viewpoint that the regulatory mechanism of phenotype expression is affected not by a nucleotide sequence but by an acquired function, i.e., the viewpoint of epigenetics, cytosine methylation is a very important phenomenon.

In this connection, it is necessary to measure immediately a position in DNA at which methylation occurs and evaluate whether the amount of the methylation is normal or not. In particular, when DNA methylation is measured in the field of medical therapeutics, rapid and accurate obtainment of measurement results is required.

As a conventional method for detecting methylcytosine (5-methylcytosine), a method based on treatment with metabisulfite salt is known. According to the method based on treatment with metabisulfite salt, DNA as a test sample is treated with metabisulfite salt and subjected to PCR and sequencing process. As a result, the methylated cytosine and non-methylated cytosine are detected as cytosine and thymine, respectively. The detection based on treatment with metabisulfite salt is disclosed, for example, in Patent Document 1 (Japanese Patent Application National Publication (Laid-Open) No. 2004-511235). However, the treatment with metabisulfite salt is disadvantageous in that a long period of time is required for heating reaction and a non-specific damage occurs in most of genome samples so that an error is produced due to the damage (erroneous detection).

As a conventional method for detecting methylcytosine, in addition to the method based on treatment with metabisulfite salt, a method using a restriction enzyme which is sensitive to methylcytosine and a restriction enzyme which is insensitive to methylcytosine has been known (MIAMI method). According to this method, a restriction enzyme which is sensitive to methylcytosine and a restriction enzyme which is insensitive to methylcytosine are used separately, and the detection is carried out by using PCR, etc. However, as being based on an enzyme reaction, it is disadvantageous in that operational process is cumbersome and it takes several days to accomplish the detection.

Patent Document 1: Japanese Patent Application National Publication (Laid-Open) No. 2004-511235

DISCLOSURE OF THE INVENTION

Problems to be Solved by the Invention

As described in the above, the conventional method which is known as a method for detecting methylated cytosine (methylcytosine) in DNA separately from non-methylated cytosine is not satisfactory in terms of fastness, convenience and high sensitivity. Thus, there has been a demand for a method which can detect methylcytosine in DNA rapidly, conveniently, and with high sensitivity.

Thus, an object of the present invention is to provide a method for detecting methylcytosine in DNA rapidly, conveniently, and with high sensitivity.

Further, another object of the present invention is to provide a compound (probe for detection, a detection agent) which can be used for the method for detecting methylcytosine rapidly, conveniently, and with high sensitivity.

Means for Solving the Problems

Inventors of the present invention have extensively studied to develop a method for detecting methylated cytosine (methylcytosine) in DNA separately from non-methylated cytosine, and as a result found that the nucleic acids having a group represented by the Formula (I), (II), (III) or (IV) described below as a base moiety can be photocoupled to methylated cytosine (methylcytosine) in DNA with high selectivity via a vinyl group bonded to a hydrophobic group, and by using this property, methylated cytosine (methylcytosine) can be detected separately from non-methylated cytosine, and therefore accomplished the present invention.

Thus, the present invention is directed to the following [1] to [10].

[1] Nucleic acids having a group represented by the Formula (I), (II), (III) or (IV) as a base moiety (the nucleic acids include a nucleic acid, a mononucleotide and a peptide nucleic acid)

[Chemical Formula 1]

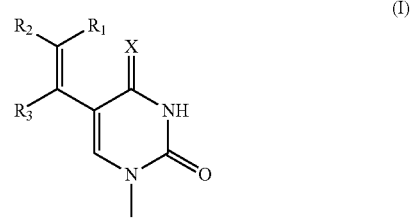

(in the Formula I, X represents O, S or NH,

R1 and R3 each independently represent hydrogen, a C1 to C6 alkyl group, a C1 to C6 alkoxy group, a cyano group or a C1 to C6 acyl group, and R2 represents a hydrophobic group having C1 to C12 carbon atoms.)

[Chemical Formula 2]

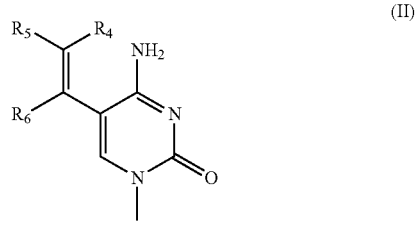

(in the Formula II, R4 and R6 each independently represent hydrogen, a C1 to C6 alkyl group, a C1 to C6 alkoxy group, a cyano group or a C1 to C6 acyl group, and R5 represents a hydrophobic group having C1 to C12 carbon atoms.)

[Chemical Formula 3]

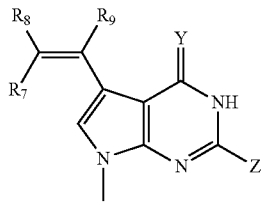

(III)

(in the Formula III, Y represents O, S or NH,
Z represents NH$_2$ when Y is O or S, or a hydrogen atom when Y is NH,
R7 and R9 each independently represent hydrogen, a C1 to C6 alkyl group, a C1 to C6 alkoxy group, a cyano group or a C1 to C6 acyl group, and
R8 represents a hydrophobic group having C1 to C12 carbon atoms.)

[Chemical Formula 4]

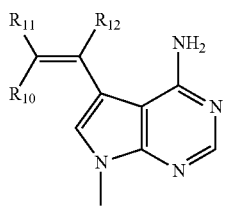

(IV)

(in the Formula IV, R10 and R12 each independently represent hydrogen, a C1 to C6 alkyl group, a C1 to C6 alkoxy group, a cyano group or a C1 to C6 acyl group, and
R11 represents a hydrophobic group having C1 to C12 carbon atoms.).

[2] The nucleic acids according to [1], wherein R2, R5, R8 and R11 are a hydrocarbon group having C1 to C12 carbon atoms (the nucleic acids include a nucleic acid, a mononucleotide and a peptide nucleic acid).

[3] An agent for photocoupling methylcytosine including the nucleic acids according to [1] or [2].

[4] A photoresponsive agent for detecting methylcytosine including the nucleic acids according to [1] or [2].

[5] A method of photocoupling methylcytosine by using the nucleic acids according to [1] or [2].

[6] A method for detecting methylcytosine by using the nucleic acids according to [1] or [2].

[7] A method for detecting methylcytosine in test nucleic acid, including:
hybridizing a nucleic acid or a peptide nucleic acid immobilized on a carrier and a test nucleic acid having methylcytosine to a template nucleic acid or a template peptide nucleic acid, wherein the nucleic acid or peptide nucleic acid has a group represented by the Formula (I), (II), (III) or (IV) as a base moiety at end according to [1] or [2];
performing light irradiation on the test nucleic acid and the immobilized nucleic acid or peptide nucleic acid that are arranged closely by the hybridization to the template nucleic acid or template peptide nucleic acid, and photocoupling the test nucleic acid to the immobilized nucleic acid or peptide nucleic acid;
removing the hybridized template nucleic acid or template peptide nucleic acid by dissociation;
hybridizing the test nucleic acid which is coupled to the immobilized nucleic acid or peptide nucleic acid to a labeled nucleic acid or a labeled peptide nucleic acid having a label site as a nucleic acid or a peptide nucleic acid capable of hybridizing to the test nucleic acid; and
detecting the label site included in the labeled nucleic acid or the labeled peptide nucleic acid.

[8] The method according to [7], wherein the template nucleic acid or the template peptide nucleic acid has a sequence which is capable of hybridizing to part or whole sequence of the immobilized nucleic acid or peptide nucleic acid and a sequence which is capable of hybridizing to part or whole sequence of the test nucleic acid, and
the sequences capable of hybridization are a sequence by which methylcytosine of the test nucleic acid and the group represented by the Formula (I), (II), (III) or (IV) of the immobilized nucleic acid or peptide nucleic acid are arranged closely (adjacently) when the immobilized nucleic acid or peptide nucleic acid is hybridized to the test nucleic acid.

[9] The method according to [7] or [8], wherein the label site is labeled with a label selected from the group consisting of a fluorescent pigment, biotin, a hapten, an enzyme, ferrocene, a spin-active compound and a radio-active compound.

[10] A kit for detecting methylcytosine including:
a nucleic acid or a peptide nucleic acid immobilized on a carrier, wherein the nucleic acid or peptide nucleic acid has a group represented by the Formula (I), (II), (III) or (IV) as a base moiety at end according to [1] or [2];
a template nucleic acid or a template peptide nucleic acid; and
a labeled nucleic acid or a labeled peptide nucleic acid having a label site.

Effect of the Invention

According to the present invention, methylated cytosine (methylcytosine) in DNA can be detected separately from non-methylated cytosine in a rapid and convenient manner with high sensitivity. According to the present invention, as the detection of methylcytosine is accomplished by selective photocoupling, the operation required for coupling can be carried out by a simple process of irradiation with light: As such, a complex operation like treatment with metabisulfite or treatment with a restriction enzyme used in conventional technology is unnecessary. Furthermore, according to the present invention, as the detection of methylcytosine is carried out by selective photocoupling, coupling is achieved by very fast photochemical reaction, and therefore the detection can be made in very short period of time compared to the treatment with metabisulfite or the treatment with a restriction enzyme that are employed by conventional technology. Furthermore, according to the present invention, a non-specific damage will not occur in a genome sample, and therefore an error due to the damage (erroneous detection) will not occur either.

The photocoupling of the present invention is a reversible photocoupling. The covalent bond which is generated by the photocoupling of the present invention may be subjected to photocleavage by irradiating with light which has a wavelength different from the wavelength used for the photocoupling. Thus, even when a DNA is photocoupled for detection of methylcytosine, after carrying out the detection for determining the presence or absence of methylation on cytosine at a specific site, the photocoupled DNA may be subjected to photocleavage for liberation. Specifically, according to the present invention, detection of methylcytosine can be achieved without damaging at all the DNA contained in a test sample both before and after detection. The present invention enables for the first time such non-destructive detection of methylcytosine.

According to the present invention, as the presence or absence of cytosine methylation at a specific site can be detected without damaging at all the DNA in a test sample, detection of the presence or absence of cytosine methylation can be also made at an another site by repeated use of the same molecule. In other words, according to the present invention, even with a single DNA molecule, detection of the presence or absence of cytosine methylation can be made over the entire molecule by repeated use of the DNA without damaging it. Therefore, detection with very high sensitivity can be achieved. In addition, according to conventional method for detecting methylcytosine, it is only possible to obtain information regarding the presence or absence of cytosine methylation at multiple sites as information for a group of homologous DNA molecules. However, according to the present invention, information regarding the presence or absence of methylation on cytosine at multiple sites can be obtained as information of a specific single DNA molecule. That is, the present invention enables for the first time the obtainment of information regarding the presence or absence of methylation of cytosine at multiple sits in a specific single DNA molecule.

As the detection of methylcytosine according to the present invention is rapid, convenient, and highly sensitive, it is highly useful when it is used in the field of medical therapeutics. From the viewpoint of rapidness, the detection of methylcytosine according to the present invention is suitable for one-day diagnosis. From the viewpoint of convenience, it enables the implementation in a broad range of health facilities. Furthermore, from the viewpoint of high sensitivity, it dramatically reduces a physical burden on a patient who provides a test sample.

BRIEF DESCRIPTION OF THE DRAWINGS

FIG. 1 illustrates selectivity of photocoupling by the photocoupling nucleic acids relating to the present invention to cytosine (C) or methylcytosine (mC), as determined by fluorescence intensity.

BEST MODE FOR CARRYING OUT THE INVENTION

Herein below, the present invention will be explained in detail in view of the embodiments. However, the present invention is not limited to the embodiments that are exemplified below.

According to the present invention, by photocoupling (photolinking) methylcytosine using the nucleic acids having a group represented by the Formula (I), (II), (III) or (IV) as a base moiety as an agent for photocoupling (photolinking) methylcytosine (a methylcytosine photocoupler or a methylcytosine photolinker), detection of methylcytosine can be made (the nucleic acids include a nucleic acid, a mononucleotide and a peptide nucleic acid).

[Chemical Formula 5]

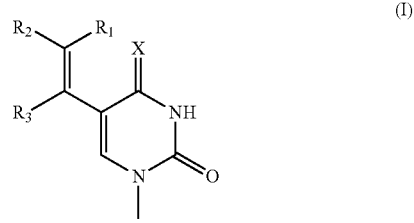

(I)

(in the Formula I, X represents O, S or NH,

R1 and R3 each independently represent hydrogen, a C1 to C6 alkyl group, a C1 to C6 alkoxy group, a cyano group or a C1 to C6 acyl group, and R2 represents a hydrophobic group having C1 to C12 carbon atoms.)

[Chemical Formula 6]

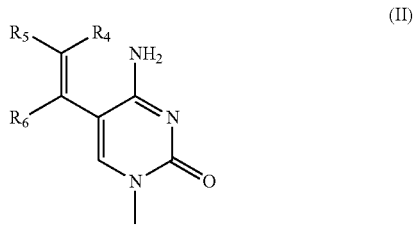

(II)

(in the Formula II, R4 and R6 each independently represent hydrogen, a C1 to C6 alkyl group, a C1 to C6 alkoxy group, a cyano group or a C1 to C6 acyl group, and R5 represents a hydrophobic group having C1 to C12 carbon atoms.)

[Chemical Formula 7]

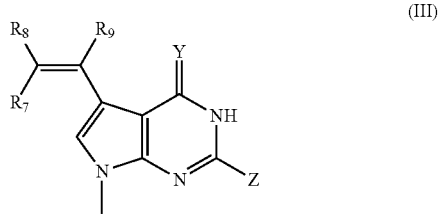

(III)

(in the Formula III, Y represents O, S or NH,

Z represents $NH_2$ when Y is O or S, or a hydrogen atom when Y is NH,

R7 and R9 each independently represent hydrogen, a C1 to C6 alkyl group, a C1 to C6 alkoxy group, a cyano group or a C1 to C6 acyl group, and R8 represents a hydrophobic group having C1 to C12 carbon atoms.)

[Chemical Formula 8]

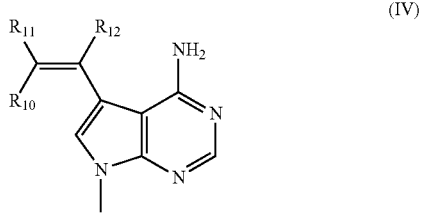

(IV)

(in the Formula IV, R10 and R12 each independently represent hydrogen, a C1 to C6 alkyl group, a C1 to C6 alkoxy group, a cyano group or a C1 to C6 acyl group, and R11 represents a hydrophobic group having C1 to C12 carbon atoms.).

That is, the nucleic acids having a group represented by the Formula (I), (II), (III) or (IV) as a base moiety may be used as a photoresponsive agent for detecting methylcytosine (a photoresponsive methylcytosine detector) (the nucleic acids include a nucleic acid, a mononucleotide and a peptide nucleic acid).

R2, R5, R8 and R11 are a hydrogen atom or a hydrophobic group having C1 to C12 carbon atoms. By having a hydrophobic group bonded to a vinyl group, photocoupling (photolinking) with high selectivity is achieved when cytosine is methylated. Therefore, the hydrophobic group is not limited to a hydrocarbon group and it may be any hydrophobic group having C1 to C12 carbon atoms. Examples thereof include a group containing a nitrogen atom, an oxygen atom or a sulfur atom, and it may form a ring structure and may be a saturated or unsaturated group.

According to the preferred embodiment of the present invention, R2, R5, R8 and R11 may be a hydrocarbon group which has C1 to C12, preferably C1 to C10, more preferably C1 to C8, still more preferably C1 to C6, still further more preferably C2 to C6, yet still furthermore preferably C3 to C6, and most preferably C4 to C6 carbon atoms. The hydrocarbon group may be a linear chain, may have a branch or may form a ring structure. The hydrocarbon group may be a saturated or unsaturated hydrocarbon group. Examples of the unsaturated hydrocarbon group which may be suitably used include a methyl group (methan-1-yl), an ethyl group (ethan-1-yl), propan-1-yl, propan-2-yl, butan-1-yl, butan-2-yl, pentan-1-yl, pentan-2-yl, pentan-3-yl, methylpropan-1-yl, methylpropan-2-yl, 2-methylbutan-1-yl, 2-methylbutan-2-yl, 2-methylbutan-3-yl, 2-methylbutan-4-yl, hexan-1-yl, hexan-2-yl, hexan-3-yl, 2-methylpentan-1-yl, 2-methylpentan-2-yl, 2-methylpentan-3-yl, 2-methylpentan-4-yl, 2-methylpentan-5-yl, 3-methylpentan-1-yl, 3-methylpentan-2-yl, 3-methylpentan-3-yl, 2,2-dimethylbutan-1-yl, 2,2-dimethylbutan-3-yl, 2,2-dimethylbutan-4-yl, 2,3-dimethylbutan-1-yl and 2,3-dimethylbutan-2-yl, etc. Examples of the cyclic saturated or unsaturated hydrocarbon group which may be suitably used include cyclohexan-1-yl, cyclohexen-1-yl, cyclohexen-3-yl, cyclohexen-4-yl, and phenyl, etc.

R1, R3, R4, R6, R7, R9, R10 and R12 each independently represent a hydrogen atom, an alkyl group, an alkoxy group, a cyano group or a C1 to C6 acyl group. Examples of the suitable alkyl group include an alkyl group which generally has C1 to C8, preferably C1 to C6, more preferably C1 to C5, further more preferably C1 to C4, still further more preferably C1 to C3, yet still further more preferably C1 to C2, and most preferably C1 carbon atom (s). Examples of the suitable alkoxy group include an alkoxy group which generally has C1 to C8, preferably C1 to C6, more preferably C1 to C5, further more preferably C1 to C4, still further more preferably C1 to C3, yet still further more preferably C1 to C2, and most preferably C1 carbon atom (s). Examples of the suitable acyl group include an acyl group which generally has C1 to C8, preferably C1 to C6, more preferably C1 to C5, further more preferably C1 to C4, still further more preferably C1 to C3, yet still further more preferably C1 to C2, and most preferably C1 carbon atom(s).

According to the particularly preferred embodiment of the present invention, R1, R3, R4, R6, R7, R9, R10 and R12 each independently represent a hydrogen, a methyl group, an ethyl group, a methoxy group, an ethoxy group, a cyano group, or an acetyl group, and preferably a hydrogen, a methyl group, a methoxy group or a cyano group.

The nucleic acids according to the present invention include, for example, a nucleic acid and a peptide nucleic acid (PNA), as well as a mononucleotide. The mononucleotides include mononucleotide of a ribonucleotide and mononucleotide of a deoxyribonucleotide. The nucleic acids include, for example, natural nucleic acids like DNA and RNA and modified nucleic acids like LNA (BNA), etc., which are non-natural (artificial) nucleic acids.

Detection of methylcytosine according to the present invention may be performed by the method for detecting methylcytosine in test nucleic acids including the steps of:

hybridizing a nucleic acid or a peptide nucleic acid immobilized on a carrier and a test nucleic acid having methylcytosine to a template nucleic acid or a template peptide nucleic acid, wherein the nucleic acid or peptide nucleic acid has a group represented by the Formula (I), (II), (III) or (IV) as a base moiety at end;

performing light irradiation on the test nucleic acid, the immobilized nucleic acid or peptide nucleic acid that are arranged closely by the hybridization to the template nucleic acid or template peptide nucleic acid, and photocoupling the test nucleic acid to the immobilized nucleic acid or peptide nucleic acid;

removing the hybridized template nucleic acid or template peptide nucleic acid by dissociation;

hybridizing the test nucleic acid which is coupled to the immobilized nucleic acid or peptide nucleic acid to a labeled nucleic acid or a labeled peptide nucleic acid having a label site as a nucleic acid or a peptide nucleic acid capable of hybridizing to the test nucleic acid; and detecting the label site included in the labeled nucleic acid or the labeled peptide nucleic acid.

By performing the method above, methylated cytosine (methylcytosine) in DNA may be detected rapidly, conveniently, and with high sensitivity, separate from non-methylated cytosine.

According to the preferred embodiment of the present invention, it is preferable that, the template nucleic acid or the template peptide nucleic acid has a sequence which is capable of hybridizing to part or whole sequence of the immobilized nucleic acid or peptide nucleic acid and a sequence which is capable of hybridizing to part or whole sequence of the test nucleic acid, and the sequences capable of hybridization are a sequence by which methylcytosine of the test nucleic acid and the group represented by the Formula (I), (II), (III) or (IV) of the immobilized nucleic acid or peptide nucleic acid are arranged closely (adjacently) when the immobilized nucleic acid or peptide nucleic acid is hybridized to the test nucleic acid.

One embodiment of the above-described preferable implementation is shown in Scheme (2) that will be described below. According to the left drawing of Scheme (2), a nucleic acid or a peptide nucleic acid immobilized on a carrier as a nucleic acid or peptide nucleic acid having a group represented by the Formula (I), (II), (III) or (IV) as a base moiety at end, a template nucleic acid or a template peptide nucleic acid, and a test nucleic acid having methylcytosine are prepared, and by having them under the condition which allows formation of a hybrid (hybridization), a hybrid is formed (hybridized).

In the left drawing of Scheme (2), the base having a group represented by the Formula (I), (II), (III) or (IV) is expressed as X. A nucleic acid having X at 5' end is immobilized on a carrier at the other end. It is not necessary to carry out the immobilization at the end as illustrated. It may be carried out through the middle region of a sequence. To enhance the efficiency of the hybridization, coupling to the carrier may be carried out via a linker having appropriate length. The linker may be nucleic acids, as well as other polymers. For the coupling between the linker and the carrier, a means known in the art may be used. The carrier is preferably a glass plate or a plastic plate. It is possible that a number of nucleic acids are immobilized by spotting them with an appropriate distance on a light-transmitting plate which is suitable for measurement by fluorescence measurement apparatus. Alternatively, it is also possible to use a plate having many light-transmitting wells, which is suitable for measurement by fluorescence measurement apparatus.

In the left drawing of Scheme (2), the target cytosine, which is to be determined in terms of the presence of absence of methylation, is any one of methylcytosine (mC) and cytosine (C), and it is expressed as Y. When methylcytosine is detected by the present invention, Y corresponds to methylcytosine. A nucleic acid which includes Y in its sequence is a test nucleic acid.

In the left drawing of Scheme (2), the template nucleic acid (the template) has a complementary sequence which can form a hybrid (hybridize) with part of the nucleic acid having X at end and with part of the test nucleic acid having Y in the sequence. Detailed information of the sequence is shown in Table 1. In Scheme (2), according to hybridization with the template nucleic acid, X of the nucleic acid having X at end and Y of the test nucleic acid are arranged closely to each other. As the role of the template nucleic acid is to arrange closely X and Y, sequence of the template nucleic acid may be any one which allows such arrangement. If such close arrangement is allowed, sequence of the template nucleic acid may be complementary to part or whole sequence of a nucleic acid having X at end. Furthermore, it such close arrangement is allowed, sequence of the template nucleic acid may be complementary to part or whole sequence of a test nucleic acid.

As shown in the left drawing of Scheme (2), after X and Y are arranged closely to each other, Y of the test nucleic acid is photocoupled to X of the immobilized nucleic acid or peptide nucleic acid by light irradiation. As the photocoupling is carried out based on a photoreaction, it is fast and clean at the same time as there is no risk of having a side reaction or a non-specific reaction. Furthermore, precise control of reaction condition as required for carrying out an enzyme reaction is not necessary.

The light which is irradiated for photocoupling is light having the wavelength generally in the range of 330 to 380 nm, preferably in the range of 350 to 380 nm, more preferably in the range of 350 to 370 nm, still more preferably in the range of 360 to 370 nm, and still further more preferably the wavelength of 366 nm. Particularly preferably, it is a laser beam with mono-wavelength of 366 nm.

The flow from the left drawing to the center drawing of Scheme (2) indicates a step of dissociating and removing the hybridized template nucleic acid by washing, following the light irradiation at 366 nm. The washing condition for dissociation and removal may be a condition which is generally used for dissociation of a hybrid like the above. However, as the test nucleic acid is covalently immobilized on a carrier via a nucleic acid having X at end based on the photocoupling between X and Y, the washing for dissociation and removal of a template nucleic acid may be carried out under the condition which is much stronger than the condition generally employed. As an example, for such condition, washing with water or an aqueous solution having the temperature range of 70° C. to 100° C., preferably 80° C. to 100° C., more preferably 85° C. to 100° C. or more, still more preferably 90° C. to 100° C., further still more preferably 95° C. to 100° C., and yet further still more preferably 98° C. to 100° C. can be mentioned, for example. Alternatively, boil washing under atmospheric condition can be mentioned and washing with water or an aqueous solution of this temperature for 10 seconds to 15 minutes, preferably 30 seconds to 10 minutes can be also mentioned, for example. By performing the dissociation and removal of a template nucleic acid by washing under the strong condition, the detection noise can be dramatically reduced.

Based on a photocoupling between X and Y, the test nucleic acid is covalently immobilized on a carrier via a nucleic acid having X at end. Thus, even after the template nucleic acid is dissociated and removed according to loss of hybridization, the test nucleic acid remains immobilized to the carrier. This state is shown in the center drawing of Scheme (2).

In the flow from the center drawing to the right drawing of Scheme (2), a process of hybridizing a test nucleic acid coupled to an immobilized nucleic acid to a labeled nucleic (ODN (Cy3)) having a label site as a nucleic acid capable of hybridizing to a test nucleic acid is shown. Condition for forming a hybrid (hybridization) may be any condition that is usually used in the art. ODN (Cy3) has a sequence cable of hybridizing to a test nucleic acid and one example of the sequence is described in Table 1.

Indicated in the right drawing in Scheme (2) is a state in which the test nucleic acid is covalently immobilized to a carrier via a nucleic acid having X at end based on photocoupling between X and Y and also the test nucleic acid forms a hybrid with the labeled nucleic acid (ODN (Cy3)).

The ODN (Cy3) described in the right drawing of Scheme (2) has Cy3, a fluorescent label, as a label site. For a label which may be used as a label site of a labeled nucleic acid, a known label may be used. For example, a label selected from the group consisting of a fluorescent pigment, biotin, a hapten, an enzyme, ferrocene, a spin-active compound and a radio-active compound may be used, and detection of each label may be performed by a means known in the art.

In the right drawing of Scheme (2), by finally detecting the label on the labeled nucleic acid, detection of the photocoupling between X and Y, which are closely arranged in the left drawing of Scheme (2), is achieved. Since such photocoupling to X is generated with high selectivity when Y is methylcytosine (mC), based on the detection strength of the label on the labeled nucleic acid, Y in the test nucleic acid can be detected as methylated cytosine.

In the state shown in the right drawing of Scheme (2), the test nucleic acid from which methylcytosine of Y is detected does not undergo any specific chemical modifications compared to the state shown in the left drawing of Scheme (2), except that Y is photocoupled to X. Further, after the photocoupling by light irradiation, the photocoupling of the present invention may be subjected to photocleavage by irradiating with light having a wavelength which is different from that used for the photocoupling.

In general, the irradiation light used for photocleavage is light with wavelength range of 300 to 320 nm, preferably light with wavelength range of 305 to 315 nm, and more preferably light with wavelength of 312 nm. Particularly preferably, it is laser beam having mono-wavelength of 312 nm.

As a photoreaction is utilized in the photocoupling and photocleavage, pH, temperature and salt concentration, etc. are not specifically limited. They may be carried out by light irradiation in a solution having pH, temperature and salt concentration at which a biological macromolecule such as nucleic acids is allowed to exist stably.

With photocleavage of a photocoupled part, the test nucleic acid used for detection of methylcytosine may be recovered without receiving any modification or damage. For detection of methylcytosine at other site, the test nucleic acid recovered by this method may be used again as a test sample for a method for detection relating to the present invention, or, as a nucleic acid having a specified methylation site, it may be also used as a starting material for other applications.

When the test nucleic acid is recovered by photocleavage of a photocoupled part, the immobilized nucleic acid (nucleic acid having X at 5' end) may be recovered in a state immobilized to a carrier without any modification or damage, and the recovered immobilized nucleic acid may be also used again for the detection method that is related to the present invention.

As described above, the nucleic acids of the present invention make it possible to obtain reversible photocoupling (photolinking) and may be used as a reversible photocoupling agent (a reversible photocoupler or a reversible photolinker) and a reversible photoresponsive agent for detecting methylcytosine. Thus, the detection method of the present invention has very advantageous characteristics that the reagents and the test sample for detection may be all recycled and used again in principle. Therefore, the method of the present invention has little environmental load and can save resources and energy, and is a method with very high sensitivity as the test sample can be recycled.

Further, the present invention is directed to a kit for detecting methylcytosine which includes, a nucleic acid or a peptide nucleic acid immobilized on a carrier, wherein the nucleic acid or peptide nucleic acid has a group represented by the Formula (I), (II), (III) or (IV) as a base moiety at end, a template nucleic acid or a template peptide nucleic acid, and a labeled nucleic acid or a labeled peptide nucleic acid having a label site.

The kit related to the present invention may be suitably used for the implementation of the detection method of the present invention.

EXAMPLES

Herein below, the present invention is explained in detail in view of the Examples. However, the present invention is not limited by the Examples.

[Synthesis of a Photoresponsive Nucleic Acid for Detection of Methylcytosine]

According to the pathway of Scheme (1) below, the photoresponsive nucleic acid which is used for detection of methylcytosine was synthesized.

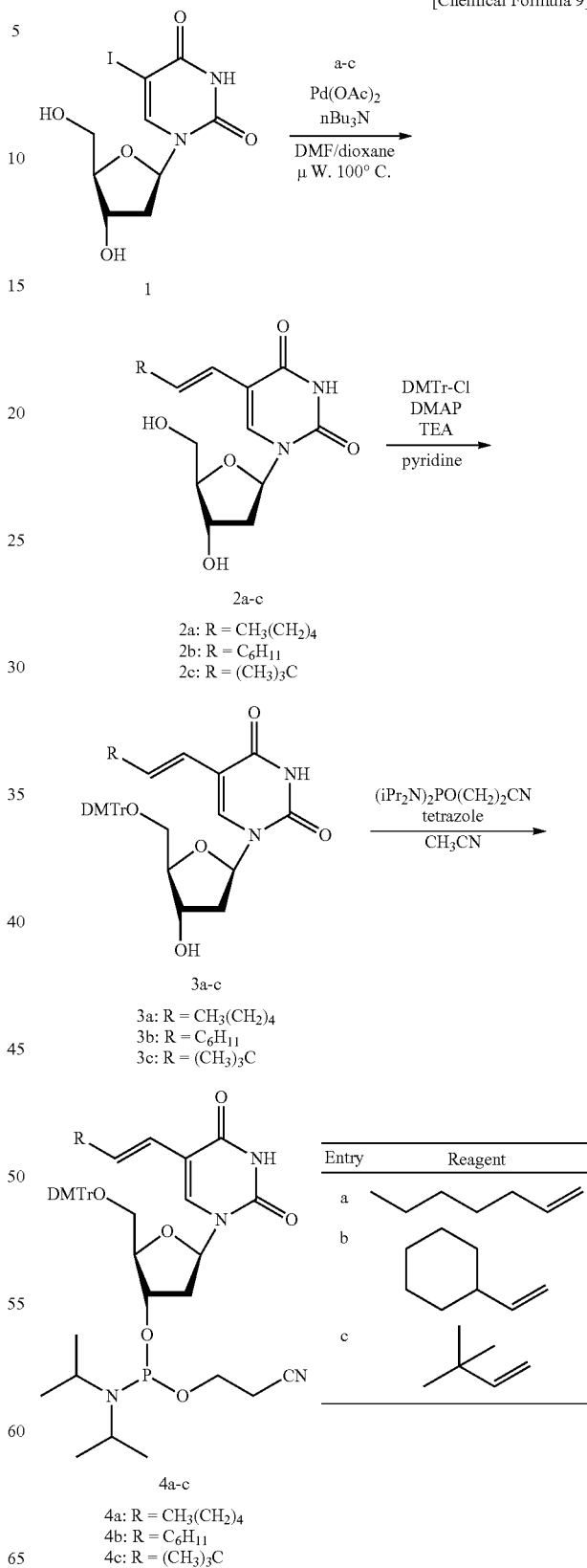

Compound 2a

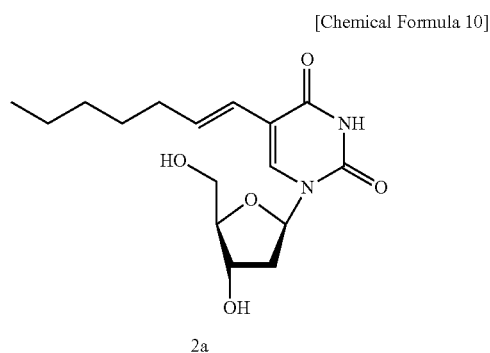

2a

Synthesis of 5-heptene-2'-deoxyuridine ($^{H}$U) (2a)

5-iodo-2'-deoxyuridine (1) (500 mg, 1.41 mmol) was dissolved in DMF (2.5 ml) and dioxane (2.5 ml), and palladium acetate (31 mg, 0.14 mmol) was added thereto to obtain a suspension. Tributylamine (340 µl, 1.41 mmol) and 1-heptene (5 ml, 3.53 mmol) were further added, and the reaction was carried out at 100° C. for 20 minutes by heating by microwaves. After confirming at least 90% decrease in the reaction materials by TLC ($CHCl_3$:MeOH=9:1), the obtained sample was purified by using a silica gel column with a development solvent of $CHCl_3$:MeOH=9:1. $^{H}$U was found to be 445 mg, 1.36 mmol and the yield was 97%. The target compound was determined by $^1$H NMR for identification. In addition, mass analysis was carried out based on MALDI-TOF MS, and it was identified as the target compound (calcd. for $C_{16}H_{25}N_2O_5$ [M+H]$^+$ 325.179, found 325.801).

$^1$H NMR (CDCl$_3$): 7.59 (s, 1H, H—C(6)); 6.29-6.13 (m, 2H, vinylic H, H—C(1')); 6.00 (d, 1H, J=16.5 vinylic H); 4.58 (m, 1H, H—C(3')); 4.03 (m, 1H, H—C(4')); 3.90-3.80 (m, 2H, H—C(5')); 2.38 (m, 2H, H—C(2')); 1.95-0.84 (m, 11H, CH$_3$(CH$_2$)$_2$).

Compound 3a

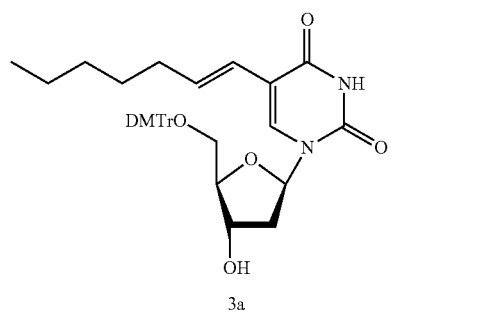

3a

Synthesis of 5-heptene-2'-deoxy-5'-O-(4,4'-dimethoxytrityl)uridine (3a)

Compound (2a) (340 mg, 1.05 mmol) was azeotroped three times with anhydrous pyridine. The mixture was added with anhydrous pyridine (2.0 ml) and 4,4'-dimethoxytrityl chloride (427 mg, 1.26 mmol) which has been deaerated for 1 hour, and subsequently with DMAP (38 mg, 0.31 mmol). Finally, triethylamine (170 µl, 1.26 mmol) was added and the mixture was stirred for 13 hours at room temperature. After characterization by TLC (CHCl$_3$:MeOH=95:5), the product was purified with silica gel column chromatography using the development solvent of CHCl$_3$ and MeOH while varying the ratio of CHCl$_3$:MeOH from 98:2 to 95:5 to obtain the target Compound (3a) as a pale yellow solid (304 mg, 0.49 mmol, yield 46%). The target compound was determined by $^1$H NMR for identification. Further, mass analysis was carried out by MALDI-TOF MS and it was identified as the target compound (calcd. for $C_{37}H_{43}N_2O_7$ [M+H]$^+$ 627.306, found 627.455).

$^1$H NMR (CDCl$_3$): 8.46 (br.s, 1H, NH); 7.63 (s, 1H, H—C(6)); 7.49-7.23 (m, 8H, arom. H); 6.87-6.82 (m, 5H, arom. H); 6.45-6.16 (m, 3H, H—C(1'), vinylic H); 4.56 (m, 1H, H—C(3')); 4.09-4.04 (m, 1H, H—C(4')); 3.76 (s, 6H, OMe); 3.53-3.33 (m, 2H, H—C(5')); 2.44-2.20 (m, 2H, H—C(2')); 1.79-1.63 (m, 11H, CH$_3$(CH$_2$)$_2$).

Compound 4a

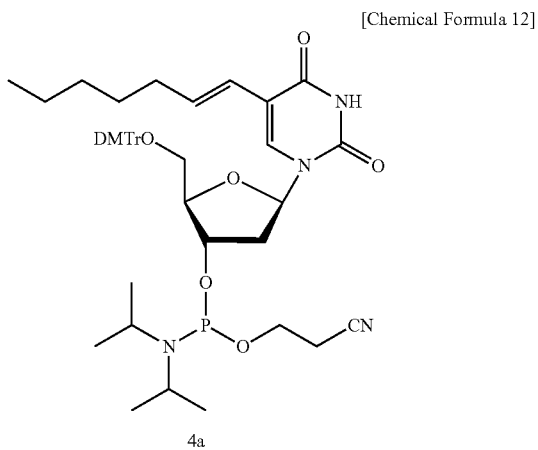

4a

Synthesis of 5-heptene-2'-deoxy-5'-O-(4,4'-dimethoxytrityl)uridine phosphoamidite (4a)

To Compound (3a) (233 mg, 0.37 mmol) which has been azeotroped with acetonitrile (0.5 ml), acetonitrile (1.5 ml) was added. To the reaction solution, 2-cyanoethyl-N,N,N',N'-tetraisopropylphosphoamidite (120 µl, 0.38 mmol) and the acetonitrile solution of 0.45 M tetrazole (910 µl, 0.41 mmol) were added, and the reaction solution was stirred at room temperature for 1.5 hours. The reaction solution was extracted three times with ethyl acetate which has been treated to remove acetic acid, and then washed with saturated aqueous solution of NaHCO$_3$. The organic layer was dried over MgSO$_4$, and the solvent was removed. The resultant was transferred to a rubber shield bottle using acetonitrile, and azeotroped three times to obtain the target Compound (4a) (product amount 320 mg, 0.39 mmol, quant). Mass analysis was carried out by MALDI-TOF MS and it was identified as the target compound (calcd. for $C_{46}H_{60}N_4O_8P$ [M+H]$^+$ 827.414, found 827.731).

Compound 2b

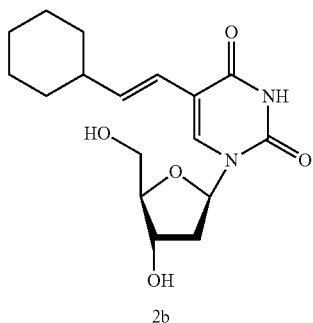

2b

Synthesis of 5-cyclohexylvinyl-2'-deoxyuridine ($^{HV}$U) (2b)

5-iodo-2'-deoxyuridine (1) (505 mg, 1.42 mmol) was dissolved in DMF (2.5 ml) and dioxane (2.5 ml), and palladium acetate (33 mg, 0.14 mmol) was added thereto to obtain a suspension. Tributylamine (340 μl, 1.41 mmol) and vinylcyclohexane (2.0 ml, 14.1 mmol) were further added to the mixture, which was heated by microwaves for the reaction at 100° C. for 20 minutes. Disappearance of the raw materials was confirmed by TLC (CHCl$_3$:MeOH=9:1). Thereafter, the purification was carried out by using a silica gel column with the development solvent of CHCl$_3$ and MeOH(CHCl$_3$:MeOH=9:1). (2b) was found to be 400 mg, 1.19 mmol and the yield was 84%. The target compound was determined by $^1$H NMR for identification. Further, mass analysis was carried out by MALDI-TOF MS and it was identified as the target compound (calcd. for $C_{17}H_{25}N_2O_5$ [M+H]$^+$ 337.176, found 337.156).

$^1$H NMR (CDCl$_3$): 7.62 (s, 1H, H—C(6)); 6.36-6.28 (m, 1H, vinylic H); 6.21-6.13 (m, 2H, vinylic H, H—C(1')); 6.03 (d, 1H, J=16.2, vinylic H); 4.61 (m, 1H, H—C(3')); 4.04 (m, 1H, H—C(4')); 3.97-3.81 (m, 2H, H—C(5')); 2.51-2.33 (m, 2H, H—C(2')); 2.14-1.06 (m, 11H, C$_6$H$_{11}$).

Compound 3b

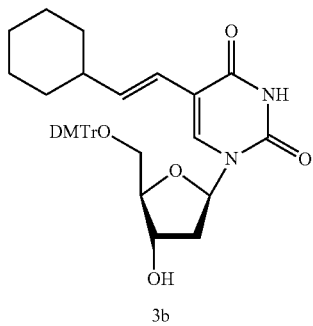

3b

Synthesis of 5-cyclohexylvinyl-2'-deoxy-5'-O-(4,4'-dimethoxytrityl)uridine (3b)

Compound (2b) (320 mg, 0.95 mmol) was azeotroped three times with anhydrous pyridine. The mixture was added with anhydrous pyridine (1.5 ml) and 4,4'-dimethoxytrityl chloride (380 mg, 1.12 mmol), and subsequently with DMAP (41 mg, 0.34 mmol). Finally, triethylamine (160 μl, 1.14 mmol) was added and the mixture was stirred for 21 hours at room temperature. After characterization by TLC (CHCl$_3$:MeOH=9:1), the product was purified using a silica gel column with the development solvent of CHCl$_3$ and MeOH while varying the ratio of CHCl$_3$:MeOH from 98:2 to 95:5 to obtain the target Compound (3b) as a pale yellow solid (329 mg, 0.52 mmol, yield 54%). The target compound was determined by $^1$H NMR for identification. Further, mass analysis was carried out by MALDI-TOF MS and it was identified as the target compound (calcd. for $C_{38}H_{43}N_2O_7$ [M+H]$^+$ 639.306, found 639.496).

$^1$H NMR (CDCl$_3$): 8.17 (br. s, 1 h, NH); 7.68 (s, 1H, H—C(6)); 7.44-7.22 (m, 8H, arom. H); 6.82 (m, 6H, arom. H, vinylic H); 6.42-6.19 (m, 2H, vinylic H, H—C(1')); 4.54(m, 1H, H—C(3')); 4.04(m, 1H, H—C(4')); 3.79 (s, 6H, OMe) 3.50 (dd, 1H, J=10.5, 3.0, H—C(5')); 2.99 (dd, 1H, J=10.5, 3.0, H—C(5')); 2.42-2.26 (m, 2H, H—C(2')); 1.99-1.22 (m, 11H, C6H$_{11}$).

Compound 4b

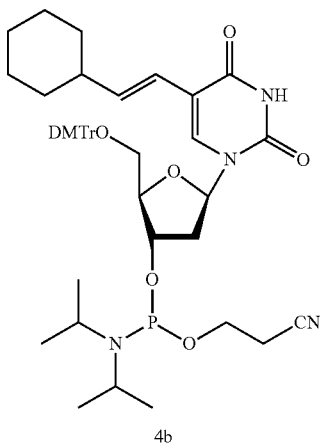

4b

Synthesis of 5-cyclohexylvinyl-2'-5'-O-(4,4'-dimethoxytrityl)uridine phosphoamidite (4b)

To Compound (3b) (320 mg, 0.50 mmol) which has been azeotroped with acetonitrile (0.5 ml), acetonitrile (2.5 ml) was added. To the reaction solution, 2-cyanoethyl-N,N,N',N'-tetraisopropylphosphoamidite (160 μl, 0.50 mmol) and the acetonitrile solution of 0.45 M tetrazole (1.2 ml, 0.55 mmol) were added, and the reaction solution was stirred at room temperature for 1.5 hours. The reaction solution was extracted three times with ethyl acetate which has been treated to remove acetic acid, and then washed with saturated aqueous solution of NaHCO$_3$. The organic layer was dried over MgSO$_4$, and the solvent was removed. The resultant was transferred to a rubber shield bottle using acetonitrile, and azeotroped three times to obtain the target Compound (4b) (product amount 432 mg, 0.51 mmol, quant.). Mass analysis was carried out by MALDI-TOF MS and it was identified as the target compound (calcd. for $C_{47}H_{60}N_4O_8P$ [M+H]$^+$ 839.414, found 839.330).

Compound 2c

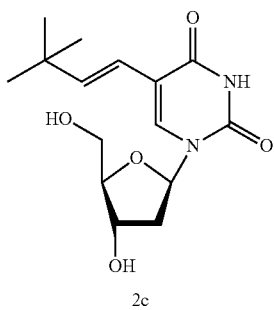

2c

Synthesis of 5-tert-butylvinyl-2'-deoxyuridine ($^{BuV}$U) (2C)

5-iodo-2'-deoxyuridine (1) (0.5 g, 1.41 mmol) was dissolved in DMF (2.5 ml) and dioxane (2.5 ml), and palladium acetate (32.0 mg, 0.14 mmol) was added thereto to obtain a suspension. Tributylamine (340 µl, 1.41 mmol) and 3,3-dimethyl-1-butene (5.5 ml, 42.3 mmol) were further added to the mixture, which was then heated by microwaves for the reaction at 100° C. for 15 minutes. Disappearance of at least 60% of the raw materials was confirmed by TLC (CHCl$_3$:MeOH=9:1), and then the reaction was terminated. Thereafter, the same process was repeated one more time for the synthesis and the purification was carried out by using a silica gel column with the development solvent of CHCl$_3$ and MeOH(CHCl$_3$:MeOH=9:1). The target Compound (2c) was obtained (271 mg, 0.87 mmol, yield 31%). The target compound was determined by $^1$H NMR for identification. Further, mass analysis was carried out by MALDI-TOF MS and it was identified as the target compound (calcd. for $C_{15}H_{23}N_2O_5$ [M+H]$^+$ 311.160, found 311.355).

$^1$H NMR (DMSO): 8.03 (s, 1H, H—C(6)); 6.44 (d, 1H, J=16.5, vinylic H); 6.17 (t, 1H, J=6.6, H—C(1')); 5.96(d, 1H, J=16.5, vinylic H); 5.24 (m, 1H, 3'-OH); 5.13 (t, 1H, J=5.0, 5'-OH); 4.25 (m, 1H, H—C(3')); 3.78 (m, 1H, H—C(4')); 3.65-3.54 (m, 2H, H—C(5')); 2.12 (m, 2H, H—C(2')); 1.59-1.49 (m, 2H, (CH$_3$)$_3$C); 1.40-1.24(m, 2H, (CH$_3$)$_3$C); 1.04(m, 5H, (CH$_3$)$_3$C).

Compound 3c

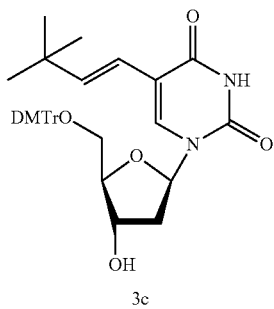

3c

Synthesis of 5-tert-butylvinyl-2'-deoxy-5'-O-(4,4'-dimethoxytrityl)uridine (3c)

Compound (2c) (497 mg, 1.60 mmol) was azeotroped three times with anhydrous pyridine. The mixture was added with anhydrous pyridine (2.0 ml), 4,4'-dimethoxytrityl chloride (666 mg, 1.97 mmol), and subsequently with DMAP (67 mg, 0.55 mmol). Finally, triethylamine (270 µl, 1.92 mmol) was added and the mixture was stirred for 19 hours at room temperature. After characterization by TLC (CHCl$_3$:MeOH=9:1), the product was purified with silica gel column chromatography using the development solvent of CHCl$_3$ and MeOH while varying the ratio of CHCl$_3$:MeOH from 97:3 to 95:5 to obtain the target Compound (3c) as a pale yellow solid (601 mg, 0.98 mmol, yield 61%). The target compound was determined by $^1$H NMR for identification. Further, mass analysis was carried out by MALDI-TOF MS and it was identified as the target compound (calcd. for $C_{36}H_{41}N_2O_7$ [M+H]$^+$ 613.291, found 613.699).

$^1$H NMR (DMSO): 11.5(br. s, 1H, NH); 8.32 (s, 1H, H—C(6)); 7.43-7.22 (m, 8H, arom. H); 6.89-6.85 (m, 5H, arom. H); 6.41 (d, 1H, J=16.2, vinylic H); 6.23 (t, 1H, J=6.3, H—C(1')); 5.72 (d, 1H, J=16.2, vinylic H); 5.32 (t, 1H, J=4.5, 3'-OH); 4.26 (m, 1H, H—C(3')); 3.91(m, 1H, H—C(4')); 3.73 (s, 6H, OMe); 3.27-3.11 (m, 2H, H—C(5')); 2.35-2.25 (m, 1H, H—C(2')); 2.21-2.13 (m, 1H, H—C(2')); 0.90-0.76 (m, 9H, (CH$_3$)$_3$C).

Compound 4c

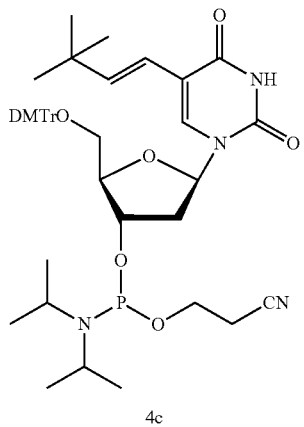

4c

Synthesis of 5-tert-butylvinyl-2'-deoxy-5'-O-(4,4'-dimethoxytrityl)uridi ne phosphoamidite (4c)

To Compound (3b) (186 mg, 0.25 mmol) which has been azeotroped with acetonitrile (0.5 ml), acetonitrile (1.5 ml) was added. To the reaction solution, 2-cyanoethyl-N,N,N',N'-tetraisopropylphosphoamidite (80 µl, 0.25 mmol) and the acetonitrile solution of 0.45 M tetrazole (600 µl, 0.27 mmol) were added, and the reaction solution was stirred at room temperature for 1.5 hours. The reaction solution was extracted three times with ethyl acetate which has been treated to remove acetic acid, and then washed with saturated aqueous solution of NaHCO$_3$. The organic layer was dried over MgSO$_4$, and then the solvent was removed. The resultant was transferred to a rubber shield bottle using acetonitrile and azeotroped three times to obtain the target Compound (4b) (product amount 197 mg, 0.24 mmol, yield 99%). Mass analysis was carried out by MALDI-TOF MS and it was identified as the target compound (calcd. for $C_{45}H_{58}N_4O_8P$ [M+H]$^+$ 813.399, found 814.770).

Synthesis of DNA

The photoresponsive nucleic acid which has been obtained according to the process in Scheme (1) was synthesized at 1 μmol scale by using ABI 3400 DNA synthesizer. After separation of CPG by using 28% aqueous ammonia solution, deprotection was carried out by incubation at 55° C. for 8 hours. Ammonia was then removed by Speed Vac. After freeze drying, the purification was carried out by HPLC to obtain ODN ($^H$U), ODN ($^{HV}$U) and ODN ($^{BuV}$U). Thereafter, mass analysis was carried out by MALDI-TOF MS.

ODN ($^H$U):      5'-$^H$UGACGTGTATCGCATTGGSSSS-NH$_2$-3'

ODN ($^{HV}$U):   5'-$^{HV}$UGACGTGTATCGCATTGGSSSS-NH$_2$-3'

ODN ($^{BuV}$U):  5'-$^{BuV}$UGACGTGTATCGCATTGGSSSS-NH$_2$-3'

Meanwhile, SSSS included in the above sequences indicates a chain structure (linker) formed by phosphoester bond of the monomer S having the following structure so as to have the phosphate group face the 5' end.

[Chemical Formula 19]

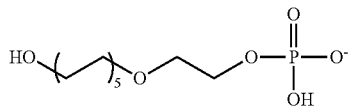

calcd. for ODN ($^H$U): [(M+H)$^+$] 7185.08, found 7184.36.
calcd. for ODN ($^{HV}$/U): [(M+H)$^+$] 7197.09, found 7197.59.
calcd. for ODN ($^{BuV}$U): [(M+H)$^+$] 7171.05, found 7171.20.

[Detection of methylcytosine]

By using the sequences that are shown in the following Table 1, detection of methylcytosine on a glass plate was carried out according to the process of the Scheme (2).

TABLE 1

| | Sequences (5'-3') |
|---|---|
| ODN ($^H$U) | $^H$UGACGTGTATCGCATTGGSSSSNH$_2$ |
| ODN ($^{HV}$U) | $^{HV}$UGACGTGTATCGCATTGGSSSSNH$_2$ |
| ODN ($^{BuV}$U) | $^{BuV}$UGACGTGTATCGCATTGGSSSSNH$_2$ |
| target (C) | GCTATCTGAGCAGCGCTCATGGTGGGGCA |
| | GCGCCTCACAACCTCCGTCATGTGCTGTGA |
| target ($^m$C) | GCTATCTGAGCAGCGCTCATGGTGGGGCA |
| | G$^m$CGCCTCACAACCTCCGTCATGTGCTGTGA |
| template | CGATACACGTCAGCTGCCCCCCACCA |
| ODN (Cy3) | Cy3-CGCTGCTCAGATAGC |

Scheme (2)

[Chemical Formula 20]

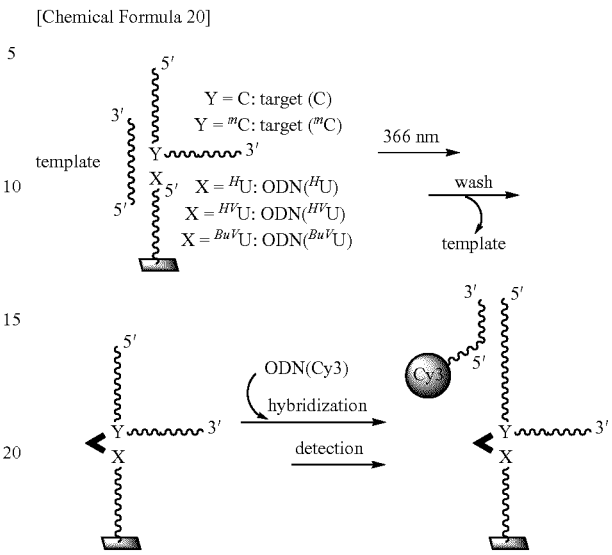

(1) Immobilization of a Photoresponsive Probe

An aqueous solution including 2 μM ODN ($^H$U), 50 mM sodium cacodylate and 100 mM NaCl was prepared. For ODN ($^{HV}$U) and ODN ($^{BuV}$U) the same aqueous solution was prepared, respectively.

The solution was spotted in an amount of 2.0 μl each on a glass plate and maintained for 16 hours for immobilization on the plate. Upon the completion of the immobilization, the plate was washed twice with an aqueous solution of 0.1% SDS (w/v), followed by washing two more times with ultra pure water. To the glass plate which has been dried at room temperature, a solution in which NaBH$_4$ (3.75 mg) is dissolved in PBS (phosphate buffered saline solution: pH 7.2) (1.5 ml) and ethanol (375 μl) was applied over the entire surface of the plate, which was then kept for 5 minutes. Thereafter, the plate was washed with ultra pure water and heated with hot water of 98° C. for 3 minutes. After the heating, it was dried at room temperature.

(2) Photocoupling Reaction on a Glass Substrate

An aqueous solution including 10 μM target (C), 10 μM template, 50 mM sodium cacodylate and 100 mM NaCl was prepared, and then spotted (4.0 μl each) on an area of the glass plate prepared from above (1) to which the photoresponsive probe is immobilized. Regarding target ($^m$C), the same aqueous solution was prepared and spotted (4.0 μl each). The glass plate was subjected to light illumination (366 nm) for 1 hour by using a transilluminator. After the light illumination, it was heated for 5 minutes with hot water of 98° C. to wash off the unreacted target (C) and target ($^m$C) as well as the template.

(3) Fluorescence Detection by Using ODN (Cy3)

An aqueous solution including 5 μM ODN (Cy3), 10 μM template, 50 mM sodium cacodylate and 100 mM NaCl was prepared. This solution was spotted (50 μl) on the glass plate of above (2) and, by placing a cover glass on top of the plate, the solution was allowed to spread over the entire surface of the plate. Hybridization was induced by incubation at 4° C. for 24 hours. After the hybridization, the plate was placed in a vessel filled with the washing liquid 1 (1×SSC, 0.2% SDS) while the cover glass still attached, and then shaken briefly until the cover glass is separated off. Another vessel was filled with the washing liquid 1, added with the plate from which the cover glass is removed, and kept at room temperature for 5 minutes under mild shaking. Another vessel was filled with the washing liquid 2 (0.1×SSC, 0.2% SDS), added with the plate, and kept at room temperature for 5 minutes under mild shaking. The same procedure was repeated with another vessel. Still another vessel was filled with the washing liquid 3 (0.1×SSC), added with the plate, and kept at room temperature for 1 minute under mild shaking. The same procedure was repeated with another vessel. Finally, the plate was briefly immersed in a beaker containing Milli Q for washing. Water was removed by using a plate spinner, and then the fluorescence detection was performed using a plate reader.

[Result]

The result obtained from the reading of the fluorescence intensity by plate reader is shown in FIG. 1(a). Comparison of the intensity between target (C) and target ($^mC$) is shown in FIG. 1(b). Every structure of ODN ($^HU$), ODN ($^{HV}U$) and ODN ($^{BuV}U$) showed efficiency of coupling to methylcytosine that is high enough to be detected. When the fluorescence intensity ratio of the of target (C) over target ($^mC$) is obtained for a case in which ODN ($^HU$) is used, the fluorescence intensity of methylcytosine (mC) was 4.2 times higher compared to the fluorescence intensity of cytosine (C). For a case in which ODN ($^{HV}U$) is used, the fluorescence intensity of methylcytosine (mC) was 4.1 times higher compared to the fluorescence intensity of cytosine (C), and for a case in which ODN ($^{BuV}U$) is used, the fluorescence intensity of methylcytosine (mC) was 2.6 times higher compared to the fluorescence intensity of cytosine (C).

As shown in the above, it was found that fluorescence intensity of methylcytosine (mC) is much higher than the fluorescence intensity of cytosine (C) for every structure of ODN ($^HU$), ODN ($^{HV}U$) and ODN ($^{BuV}U$). From this result, it was determined that, when the photocoupling nucleic acids of the present invention are used, photocoupling to methylcytosine (mC) occurs with very high efficiency compared to photocoupling to cytosine (C), thus indicating that the photocoupling occurs selectively for methylated cytosine.

Industrial Applicability

According to the present invention, methylated cytosine (methylcytosine) in DNA can be detected rapidly, conveniently, and with high sensitivity, separate from the non-methylated cytosine, and therefore it is industrially very useful. The present invention enables for the first time the non-destructive detection of methylcytosine, and thus enables for the first time the obtainment of information regarding the presence or absence of methylation on cytosine at multiple sites in a certain single DNA molecule. Detection of methylcytosine by the present invention is very useful even when it is employed in the field of medical therapeutics, and as being rapid and convenient, it is appropriate for one-day diagnosis and can be implemented in a broad range of medical facilities, respectively. Further, as having high sensitivity, it can dramatically reduce a physical burden on a patient who provides a test sample.

The invention claimed is:

1. A method of photocoupling methylcytosine by using nucleic acids, comprising:

hybridizing both (i) a nucleic acid or a peptide nucleic acid immobilized on a carrier, and (ii) a test nucleic acid having methylcytosine to a template nucleic acid or a template peptide nucleic acid, thereby closely arranging the nucleic acid or peptide nucleic acid immobilized on the carrier and the test nucleic acid having methylcytosine to the template nucleic acid or template peptide nucleic acid, wherein the nucleic acid or peptide nucleic acid has a group represented by the Formula (I), (II), (III) or (IV) as a base moiety at a 5' end thereof,

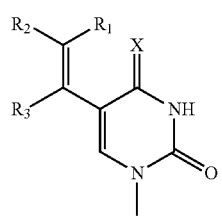

(I)

wherein in the Formula (I), X represents O, S or NH, wherein in the Formula (I), $R_1$ and $R_3$ each independently represent hydrogen, a C1 to C6 alkyl group, a C1 to C6 alkoxy group, a cyano group or a C1 to C6 acyl group, wherein in the Formula (I), $R_2$ represents a hydrophobic group having C1 to C12 carbon atoms,

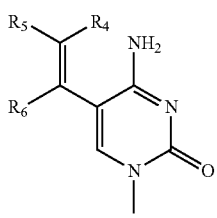

(II)

wherein in the Formula (II), $R_4$ and $R_6$ each independently represent hydrogen, a C1 to C6 alkyl group, a C1 to C6 alkoxy group, a cyano group or a C1 to C6 acyl group, wherein in the Formula (II), $R_5$ represents a hydrophobic group having C1 to C12 carbon atoms,

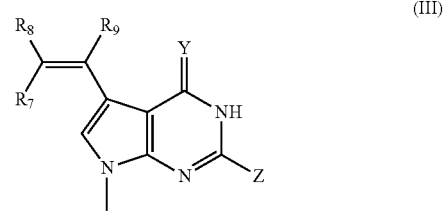

(III)

wherein in the Formula (III), Y represents O, S or NH, wherein in the Formula (III), Z represents $NH_2$ when Y is O or S, or a hydrogen atom when Y is NH, wherein in the Formula (III), $R_7$ and $R_9$ each independently represent hydrogen, a C1 to C6 alkyl group, a C1 to C6 alkoxy group, a cyano group or a C1 to C6 acyl group, wherein in the Formula (III), $R_8$ represents a hydrophobic group having C1 to C12 carbon atoms,

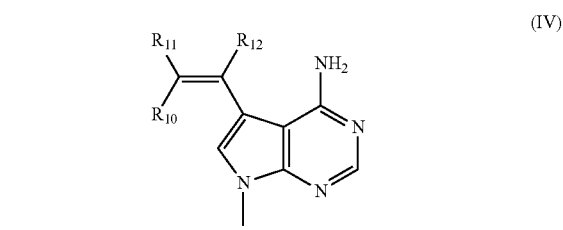

(IV)

wherein in the Formula (IV), $R_{10}$ and $R_{12}$ each independently represent hydrogen, a C1 to C6 alkyl group, a C1 to C6 alkoxy group, a cyano group or a C1 to C6 acyl group, wherein in the Formula (IV), $R_{11}$ represents a hydrophobic group having C1 to C12 carbon atoms; and performing light irradiation on the test nucleic acid and the immobilized nucleic acid or peptide nucleic acid that are arranged closely by the hybridization to the template nucleic acid or template peptide nucleic acid, thereby photocoupling the test nucleic acid to the immobilized nucleic acid or peptide nucleic acid.

2. A method for detecting methylcytosine in test nucleic acid, comprising:

hybridizing both (i) a nucleic acid or a peptide nucleic acid immobilized on a carrier, and (ii) a test nucleic acid having methylcytosine to a template nucleic acid or a template peptide nucleic acid, thereby closely arranging the nucleic acid or peptide nucleic acid immobilized on the carrier and the test nucleic acid having methylcytosine to the template nucleic acid or template peptide nucleic acid, wherein the nucleic acid or peptide nucleic acid has a group represented by the Formula (I), (II), (III) or (IV) as a base moiety at a 5' end thereof,

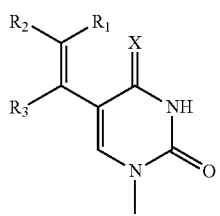

(I)

wherein in the Formula (I), X represents O, S or NH,
wherein in the Formula (I), R$_1$ and R$_3$ each independently represent hydrogen, a C1 to C6 alkyl group, a C1 to C6 alkoxy group, a cyano group or a C1 to C6 acyl group,
wherein in the Formula (I), R$_2$ represents a hydrophobic group having C1 to C12 carbon atoms,

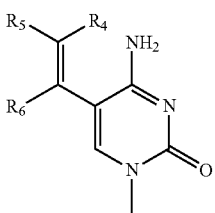

(II)

wherein in the Formula (II), R$_4$ and R$_6$ each independently represent hydrogen, a C1 to C6 alkyl group, a C1 to C6 alkoxy group, a cyano group or a C1 to C6 acyl group,
wherein in the Formula (II), R$_5$ represents a hydrophobic group having C1 to C12 carbon atoms,

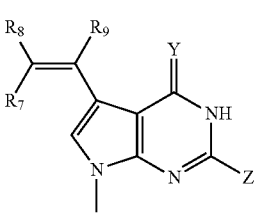

(III)

wherein in the Formula (III), Y represents O, S or NH,
wherein in the Formula (III), Z represents NH$_2$ when Y is O or S, or a hydrogen atom when Y is NH,
wherein in the Formula (III), R$_7$ and R$_9$ each independently represent hydrogen, a C1 to C6 alkyl group, a C1 to C6 alkoxy group, a cyano group or a C1 to C6 acyl group,
wherein in the Formula (III), R$_8$ represents a hydrophobic group having C1 to C12 carbon atoms,

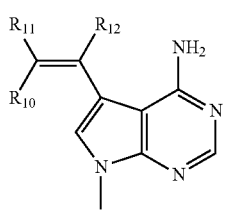

(IV)

wherein in the Formula (IV), R$_{10}$ and R$_{12}$ each independently represent hydrogen, a C1 to C6 alkyl group, a C1 to C6 alkoxy group, a cyano group or a C1 to C6 acyl group, and
wherein in the Formula (IV), R$_{11}$ represents a hydrophobic group having C1 to C12 carbon atoms;

performing light irradiation on the test nucleic acid and the immobilized nucleic acid or peptide nucleic acid that are arranged closely by the hybridization to the template nucleic acid or template peptide nucleic acid, thereby photocoupling the test nucleic acid to the immobilized nucleic acid or peptide nucleic acid;

removing the hybridized template nucleic acid or template peptide nucleic acid by dissociation;

hybridizing the test nucleic acid, which is coupled to the immobilized nucleic acid or peptide nucleic acid, to a labeled nucleic acid or a labeled peptide nucleic acid having a label site as a nucleic acid or a peptide nucleic acid capable of hybridizing to the test nucleic acid; and detecting the label site included in the labeled nucleic acid or the labeled peptide nucleic acid.

3. The method according to claim 2,
wherein the template nucleic acid or the template peptide nucleic acid has (i) a sequence which is capable of hybridizing to a partial or whole sequence of the immobilized nucleic acid or peptide nucleic acid, and (ii) a sequence which is capable of hybridizing to a partial or whole sequence of the test nucleic acid, and wherein (i) a methylcytosine of the test nucleic acid and (ii) the group represented by the Formula (I), (II), (III) or (IV) of the immobilized nucleic acid or peptide nucleic acid are arranged closely when the immobilized nucleic acid or peptide nucleic acid is hybridized to the test nucleic acid.

4. The method according to claim 2 or 3, wherein the label site is labeled with a label selected from the group consisting of a fluorescent pigment, biotin, a hapten, an enzyme, ferrocene, a spin-active compound and a radio-active compound.

5. A kit for detecting methylcytosine, comprising:
a nucleic acid or a peptide nucleic acid immobilized on a carrier, the nucleic acid or peptide nucleic acid having a group represented by the following Formula (I), (II), (III) or (IV) as a base moiety at a 5' end thereof:

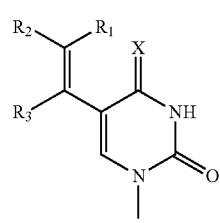

(I)

wherein in the Formula (I), X represents O, S or NH,
wherein in the Formula (I), R$_1$ and R$_3$ each independently represent hydrogen, a C1 to C6 alkyl group, a C1 to C6 alkoxy group, a cyano group or a C1 to C6 acyl group,
wherein in the Formula (I), R$_2$ represents a hydrophobic hydrocarbon group having C1 to C12 carbon atoms,

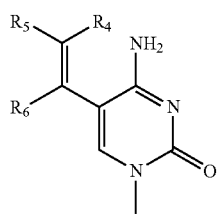

(II)

wherein in the Formula (II), $R_4$ and $R_6$ each independently represent hydrogen, a C1 to C6 alkyl group, a C1 to C6 alkoxy group, a cyano group or a C1 to C6 acyl group, wherein in the Formula (II), $R_5$ represents a hydrophobic hydrocarbon group having C1 to C12 carbon atoms,

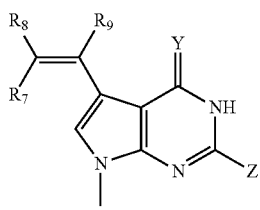

(III)

wherein in the Formula (III), Y represents O, S or NH,
wherein in the Formula (III), Z represents $NH_2$ when Y is O or S, or a hydrogen atom when Y is NH,
wherein in the Formula (III), $R_7$ and $R_9$ each independently represent hydrogen, a C1 to C6 alkyl group, a C1 to C6 alkoxy group, a cyano group or a C1 to C6 acyl group,
wherein in the Formula (III), $R_8$ represents a hydrophobic hydrocarbon group having C1 to C12 carbon atoms,

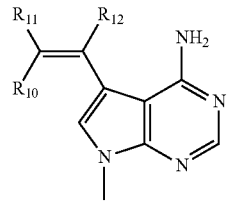

(IV)

wherein in the Formula (IV), $R_{10}$ and $R_{12}$ each independently represent hydrogen, a C1 to C6 alkyl group, a C1 to C6 alkoxy group, a cyano group or a C1 to C6 acyl group, and
wherein in the Formula (IV), $R_{11}$ represents a hydrophobic hydrocarbon group having C1 to C12 carbon atoms;
a template nucleic acid or a template peptide nucleic acid; and
a labeled nucleic acid or a labeled peptide nucleic acid having a label site.

6. The method of photocoupling methylcytosine by using nucleic acids according to claim 1, wherein $R_2$, $R_5$, $R_8$ and $R_{11}$ are each a hydrocarbon group having C1 to C12 carbon atoms.

7. The method for detecting methylcytosine in test nucleic acid according to claim 2, wherein $R_2$, $R_5$, $R_8$ and $R_{11}$ are each a hydrocarbon group having C1 to C12 carbon atoms.

* * * * *

SEQUENCE LISTING

```
<160> NUMBER OF SEQ ID NOS: 7

<210> SEQ ID NO 1
<211> LENGTH: 18
<212> TYPE: DNA
<213> ORGANISM: Artificial Sequence
<220> FEATURE:
<223> OTHER INFORMATION: probe DNA ; named ODN(HU)
<220> FEATURE:
<221> NAME/KEY: modified_base
<222> LOCATION: (1)..(1)
<223> OTHER INFORMATION: n stands for 5-heptene-2'-deoxyuridine
<220> FEATURE:
<221> NAME/KEY: misc_feature
<222> LOCATION: (18)
<223> OTHER INFORMATION: g binds to a linker having four monomers each
      represented by Chemical Formula 19, the four monomers being bound
      to each other by a phosphoester bond with the phosphate group
      facing the 5' end

<400> SEQUENCE: 1
ngacgtgtat cgcattgg                                                 18

<210> SEQ ID NO 2
<211> LENGTH: 18
<212> TYPE: DNA
<213> ORGANISM: Artificial Sequence
<220> FEATURE:
<223> OTHER INFORMATION: probe DNA ; named ODN(HVU)
<220> FEATURE:
<221> NAME/KEY: modified_base
<222> LOCATION: (1)..(1)
<223> OTHER INFORMATION: n stands for 5-cyclohexylvinyl-2'-deoxyuridine
<220> FEATURE:
<221> NAME/KEY: misc_feature
<222> LOCATION: (18)
<223> OTHER INFORMATION: g binds to a linker having four monomers each
      represented by Chemical Formula 19, the four monomers being bound
      to each other by a phosphoester bond with the phosphate group
      facing the 5' end
```

<400> SEQUENCE: 2
ngacgtgtat cgcattgg                                                 18

<210> SEQ ID NO 3
<211> LENGTH: 18
<212> TYPE: DNA
<213> ORGANISM: Artificial Sequence
<220> FEATURE:
<223> OTHER INFORMATION: probe DNA ; named ODN(BuVU)
<220> FEATURE:
<221> NAME/KEY: modified_base
<222> LOCATION: (1)..(1)
<223> OTHER INFORMATION: n stands for 5-tert-butylvinyl-2'-deoxyuridine
<220> FEATURE:
<221> NAME/KEY: misc_feature
<222> LOCATION: (18)
<223> OTHER INFORMATION: g binds to a linker having four monomers each
      represented by Chemical Formula 19, the four monomers being bound
      to each other by a phosphoester bond with the phosphate group
      facing the 5' end

<400> SEQUENCE: 3
ngacgtgtat cgcattgg                                                 18

<210> SEQ ID NO 4
<211> LENGTH: 60
<212> TYPE: DNA
<213> ORGANISM: Artificial Sequence
<220> FEATURE:
<223> OTHER INFORMATION: target DNA ; named target(C)

<400> SEQUENCE: 4
gctatctgag cagcgctcat ggtgggggca gcgcctcaca acctccgtca tgtgctgtga   60

<210> SEQ ID NO 5
<211> LENGTH: 60
<212> TYPE: DNA
<213> ORGANISM: Artificial Sequence
<220> FEATURE:
<223> OTHER INFORMATION: target DNA ; named target (mC)
<220> FEATURE:
<221> NAME/KEY: misc_feature
<222> LOCATION: (32)..(32)
<223> OTHER INFORMATION: n stands for methylcytosine

<400> SEQUENCE: 5
gctatctgag cagcgctcat ggtgggggca gngcctcaca acctccgtca tgtgctgtga   60

<210> SEQ ID NO 6
<211> LENGTH: 26
<212> TYPE: DNA
<213> ORGANISM: Artificial Sequence
<220> FEATURE:
<223> OTHER INFORMATION: template DNA

<400> SEQUENCE: 6
cgatacacgt cagctgcccc ccacca                                        26

<210> SEQ ID NO 7
<211> LENGTH: 15
<212> TYPE: DNA
<213> ORGANISM: Artificial Sequence
<220> FEATURE:
<223> OTHER INFORMATION: probe DNA ; named ODN(Cy3)

```
<220> FEATURE:
<221> NAME/KEY: modified_base
<222> LOCATION: (1)..(1)
<223> OTHER INFORMATION: n stands for Cy3-labelled Cytosine

<400> SEQUENCE: 7
ngctgctcag atagc                                               15
```